(12) United States Patent
DiCaprio et al.

(10) Patent No.: US 7,001,419 B2
(45) Date of Patent: Feb. 21, 2006

(54) STENT DELIVERY SYSTEM WITH MEMBRANE

(75) Inventors: Fernando DiCaprio, St. Paul, MN (US); Jan Seppala, Maple Grove, MN (US); Raed Rizq, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 427 days.

(21) Appl. No.: 09/970,459

(22) Filed: Oct. 2, 2001

(65) Prior Publication Data

US 2002/0116046 A1   Aug. 22, 2002

Related U.S. Application Data

(60) Provisional application No. 60/238,178, filed on Oct. 5, 2000.

(51) Int. Cl.
*A61F 2/06*  (2006.01)
(52) U.S. Cl. .................................... 623/1.11
(58) Field of Classification Search ............. 623/1.11, 623/1.12–1.2; 606/194
See application file for complete search history.

(56) References Cited

U.S. PATENT DOCUMENTS

| | | | |
|---|---|---|---|
| 4,655,771 A | 4/1987 | Wallsten | 623/1 |
| 4,732,152 A | 3/1988 | Wallsten | 128/343 |
| 4,733,665 A | 3/1988 | Palmaz | 128/343 |
| 4,740,207 A | 4/1988 | Kreamer | 623/1 |
| 4,848,343 A | 7/1989 | Wallsten | 128/343 |
| 4,875,480 A | 10/1989 | Imbert | 128/343 |
| 4,922,405 A | 5/1990 | Foll et al. | 363/126 |
| 4,950,227 A | 8/1990 | Savin | 604/8 |
| 4,954,126 A | 9/1990 | Wallsten | 600/36 |
| 5,007,926 A | 4/1991 | Derbyshire | 623/1 |
| 5,026,377 A | 6/1991 | Burton | |
| 5,061,275 A | 10/1991 | Wallsten et al. | 623/1 |
| 5,064,435 A | 11/1991 | Porter | |
| 5,071,407 A | 12/1991 | Termin | 604/104 |
| 5,078,720 A | 1/1992 | Burton | 606/108 |
| 5,108,416 A | 4/1992 | Ryan et al. | 606/194 |
| 5,201,757 A | 4/1993 | Heyn | 606/198 |
| 5,234,457 A | 8/1993 | Andersen | 606/198 |
| 5,403,341 A | 4/1995 | Solar | 606/198 |

(Continued)

FOREIGN PATENT DOCUMENTS

EP      0 712 615 A1    5/1996

(Continued)

OTHER PUBLICATIONS

Palmaz et al 156 *Radiology* 73 (1985).

*Primary Examiner*—(Jackie) Tan-Uyen T. Ho
(74) *Attorney, Agent, or Firm*—Vidas, Arrett & Steinkraus, P.A.

(57) ABSTRACT

A stent delivery system comprising a catheter. The catheter having a catheter shaft, and a balloon mounted thereto. A stent is disposed about at least a portion of the balloon. The stent having an unexpanded state and an expanded state. The stent being retained on the balloon in the unexpanded state by at least one sleeve. The at least one sleeve having a first portion engaged to the catheter and a second portion at least partially overlaying an end of the stent when the stent is in the unexpanded state. At least one membrane is disposed about a portion of the stent. The at least one membrane constructed and arranged to prevent portions of the stent thereunder from flaring out during advancement of the catheter.

15 Claims, 5 Drawing Sheets

U.S. PATENT DOCUMENTS

| | | |
|---|---|---|
| 5,944,726 A | 8/1999 | Blaeser ........................ 606/108 |
| 5,968,069 A | 10/1999 | Dusbabek et al. ........... 606/194 |
| 5,980,530 A | 11/1999 | Willard et al. ............... 606/108 |
| 6,033,433 A | 3/2000 | Ehr et al. ....................... 623/1 |
| 6,068,634 A | 5/2000 | Cornelius ................... 606/108 |
| 6,143,022 A * | 11/2000 | Shull et al. ................. 623/1.13 |
| 6,270,523 B1 * | 8/2001 | Herweck et al. ........... 623/1.13 |
| 6,379,382 B1 * | 4/2002 | Yang ......................... 623/1.42 |
| 6,607,552 B1 * | 8/2003 | Hanson ..................... 623/1.11 |

FOREIGN PATENT DOCUMENTS

| | | |
|---|---|---|
| EP | 1 034 752 A1 | 9/2000 |
| WO | 97/24080 | 7/1997 |

* cited by examiner

STENT DELIVERY SYSTEM WITH MEMBRANE

CROSS-REFERENCE TO RELATED APPLICATIONS

This application claims priority to provisional Application No. 60/238,178 filed Oct. 5, 2000 the contents of which is hereby incorporated by reference.

STATEMENT REGARDING FEDERALLY SPONSORED RESEARCH

Not Applicable

BACKGROUND OF THE INVENTION

1. Field of the Invention

This invention concerns apparatus suitable for delivery of stents to body cavities. The present invention is particularly directed to improved arrangements for releasably securing the stent to the catheter to prevent snagging of portions of the stent while the stent is being advanced through the tortuous confines of a body vessel. By way of the present invention a stent is held in place on the catheter and its ends and strut elements are kept from flaring outward by means of at least one sleeve, or sock, abutting the ends of the stent. In addition, the present invention is directed to the use of a membrane which may be disposed about a region of the stent which may be between or may overlap the portions of the stent secured by the end sleeves. Prior to stent delivery, the membrane may be retracted, may be configured so as to dissolve or otherwise degrade within the vessel, or may optionally be deployed along with the stent.

2. Description of the Related Art

Stents are tubular devices designed to maintain the patency of a bodily vessel. Stents have been used in a number of different parts of the body including the vasculature, the urinary system, the biliary ducts and the esophagus. A stent is typically delivered to a desired bodily location via a stent delivery system such as a catheter. The stent, disposed about the distal end of the catheter, is inserted in a bodily vessel and delivered to the desired bodily location where it is then deployed.

Stents may be self-expanding, mechanically expandable or hybrids. Examples of self-expanding stents include coil stents and stents made from shape memory materials such as NITINOL. One such stent is disclosed in copending, commonly assigned U.S. application Ser. No. 08/511,076. Mechanically expandable stents are most often expanded by medical balloons. Such stents are typically made of metals such as stainless steel. An example of the latter is disclosed in U.S. Pat. No. 6,033,433. Hybrid stents may be mechanically expandable in part and self-expanding in part. An example of such a stent is disclosed in copending, commonly assigned U.S. application Ser. No. 09/087,526.

Stents delivered to a restricted coronary artery, for example, may be expanded to a larger diameter by the balloon catheter, and left in place in the artery at the site of a dilated lesion are shown in U.S. Pat. No. 4,740,207 to Kreamer and U.S. Pat. No. 5,007,926 to Derbyshire.

Palmaz et al., 156 *Radiology* 73 (1985) and U.S. Pat. No. 4,733,665 describe introduction of a stent over a balloon catheter.

The stent delivery apparatus of the present invention may also utilize a self-expanding stent, which is well known in the art. A well known self-expanding stent is the woven braided stent disclosed in U.S. Pat. No. 4,655,771 (Wallsten); U.S. Pat. No. 4,954,126 (Wallsten) and U.S. Pat. No. 5,061,275 (Wallsten), although any type of self-expanding stent may be deployed using the inventive delivery system and method. The delivery system of the present invention may also be used to deliver a balloon expanded stent and may also deliver stent grafts, which are well known in the art.

As is commonly known in the art, stents may have numerous elements such as struts and other members which may flex or shift in a variety of manners during advancement of the catheter prior to stent delivery. Such flexing may result in some elements protruding outward from the catheter, which could interfere with the vessel wall or otherwise prevent further advancement of the catheter, especially in those regions of a vessel which are particularly tortuous. As a result it would be desirable to provide a covering for the stent which is extremely flexible, has a low profile and which provides sufficient coverage of the stent to prevent stent elements from protruding outward from the catheter during advancement.

The delivery systems for stents are generally comprised of catheters with the stent axially surrounding the distal end of the catheter. In many stent delivery catheters the stent is retained on the balloon catheter with a radially disposed sleeve or sheath which may be retracted or otherwise removed to release the stent. More recently stent delivery systems have included one or more stent retaining sleeves or socks disposed about the respective ends of the stent to hold the stent in the reduced configuration on the delivery catheter.

Inflation expandable stent delivery and deployment assemblies are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Other patents which describe sleeves, and material used therefor, include Blaeser et al. U.S. Pat. No. 5,944,726 issued Aug. 31, 1999; Dusbabek et al. U.S. Pat. No. 5,968,069, issued Dec. 19, 1999; and Cornelius et al., U.S. Pat. No. 6,068,634, issued May 30, 2000, both of which are incorporated by reference in their entirety.

In addition, co-pending application Ser. Nos. 08/701,979; 08/702,149; 09/273,520; 09/549,286; 09/552,807; 09/668,496; 09/664,267; 09/664,268; all relate to stent retaining sleeves or socks.

As indicated above, in addition to employing end sleeves or socks for retaining the ends of the stent on the catheter prior to stent delivery, the present invention also employs a centrally disposed sheath which may be retracted off of the stent prior to delivery or which may be expanded along with the stent into a body vessel as desired.

An example of a method and use of a sheath to retain a stent on a catheter is respectively disclosed in U.S. Pat. No. 5,071,407 (Termin) and U.S. Pat. No. 5,064,435 (Porter), both of which use a silicon rubber sheath to compress the stent on the catheter. A similar technique is disclosed in U.S. Pat. No. 5,026,377 (Burton) and U.S. Pat. No. 5,078,720 (Burton).

A variation on surrounding the stent with a sheath is disclosed in U.S. Pat. No. 4,732,152 (Wallsten); U.S. Pat. No. 4,848,343 (Wallsten) and U.S. Pat. No. 4,875,480 (Imbert), all of which disclose using a sleeve formed of a doubled-over section of membrane to compress and contain the stent.

U.S. Pat. No. 5,234,457 discloses using a sheath to surround a mesh stent of the type disclosed in U.S. Pat. No. 4,922,405. However, in this patent the sheath is not used to compress the stent, but is used to prevent fluid from accessing the stent. The stent is impregnated with a pure gelatin or other dissolvable material which, when cured, has sufficient strength to hold the stent in its reduced delivery configuration. Other examples of sheaths for use in retaining and delivery of a stent with a stent delivery catheter are known.

The use of a sheath in conjunction with a single end sleeve or sock is also known. Co-pending application Ser. Nos. 09/228,097 and 09/332,914 include the use of a stent retaining sock or sleeve which may be placed over the distal end of the stent and secured to the catheter. A sheath may be employed to cover the entire stent including the distal end.

One drawback of using a sheath to retain a stent on a catheter, is that the sheath must inherently be retracted or otherwise removed from the stent. Such retraction typically requires movement of the entire sheath or exterior catheter in order effect release of the stent. This can be seen in Wallsten U.S. Pat. No. 4,655,771 and Wallsten U.S. Pat. No. 4,954,126 in which tubular member 23 is moved forward from position 22 to position 30. In Termin U.S. Pat. No. 5,071,407 the sheath 32 is withdrawn proximally with respect to the stent. In Porter U.S. Pat. No. 5,064,435 the sheath 38 is withdrawn proximally with respect to the stent. Burton U.S. Pat. No. 5,026,377 also moves an outer sleeve backwards relative to the stent. In Wallsten U.S. Pat. No. 4,732,152; Wallsten U.S. Pat. No. 4,848,343, and Imbert U.S. Pat. No. 4,875,480, a hose 5 is connected to a maneuvering tube 8 which runs the length of the catheter. Finally, in Heyn, finger grip 5, connected to section 58 causes outer catheter 20 and sleeve 24 to move proximally relative to the stent.

In all of the cases discussed in the preceding paragraph, movement occurs over the entire length of the catheter between the proximal end controlled by the physician and the distal end where the stent is released. This catheter movement in the vessel creates several problems. First, catheter movement can disturb or move the introducer sheath at the wound site where the catheter is inserted into the vessel. Secondly, in tortuous anatomy the added friction caused by rubbing the outer catheter against the vessel, as well as the added friction created between the inner/outer layer interface, can make deployment difficult. The translation of control movements from the proximal to the distal end is imprecise, jerky and in some instances impossible due to the increased friction caused by tortuosity. Thirdly, it can create trauma to the endothelium over the entire length of the catheter.

Another drawback to the prior art stent delivery systems discussed above is that requiring an extra sheath layer, sleeve layer or layered catheters (Heyn) increases the profile of the catheter, which is undesirable. The Heyn device described in U.S. Pat. No. 5,201,757 has a profile of 0.12 inches (3.048 mm). A reduction in profile is considered significant to those skilled in the art.

In light of the above, it would be desirable to employ a stent covering which functions to help retain the stent on the catheter but which could optionally be left on the catheter during stent delivery so as to avoid damaging the stent or causing undesirable movement of the stent during sheath retraction. It would be desirable to provide for a covering which is flexible and which sufficiently covers a stent so as to prevent stent elements from protruding outward from the catheter and interfering with a vessel wall prior to delivery. It would also be desirable to provide a covering which does not increase the profile of the stent delivery catheter beyond its profile without the covering.

All US patents, applications and all other published documents mentioned anywhere in this application are incorporated herein by reference in their entirety.

BRIEF SUMMARY OF THE INVENTION

In light of the above, this invention provides for a stent delivery catheter employing one or more socks or sleeves to retain the stent on the catheter. In addition a unique membrane or stent covering is employed between the stent retaining sleeves to provide complete or selective coverage of the stent therebetween. The membrane of the present invention is sufficiently flexible to provide for adequate trackability of the catheter through the extremely tortuous confines of a body vessel. However, the membrane is of sufficient strength to prevent stent elements from lifting outward from the catheter surface thereby preventing such elements from interfering with a vessel wall during catheter advancement.

In at least one embodiment of the invention the membrane may be a single continuous membrane which covers a substantial portion of the stent between a pair of end sleeves.

In at least one embodiment of the invention the membrane may be a series of selectively placed membranes which cover selected portions of the stent.

In at least one embodiment of the invention the membrane has a thickness which is equal to or less than thickness of the stent end retaining sleeve(s) which may be between 0.001 and 0.004 inches in thickness.

In at least one embodiment of the invention, the membrane is approximately 0.002 inches thick.

In at least one embodiment of the invention the membrane may be retracted from the stent prior to stent delivery.

In at least one embodiment of the invention the membrane may be soluble.

In at least one embodiment the membrane may be used for drug delivery.

In at least one embodiment of the invention the membrane may be expanded with the stent.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
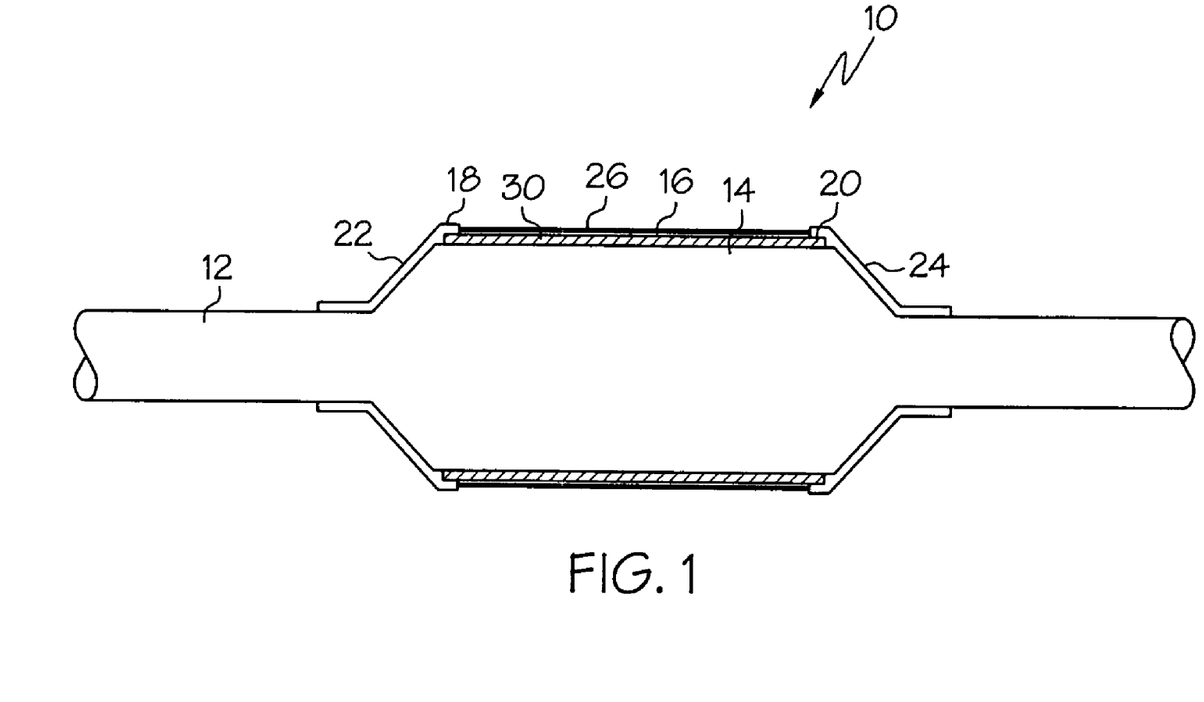
FIG. 1 is a side view of an embodiment of the invention.

As may be seen in FIG. 1, the present invention is directed to a stent delivery catheter, indicated generally at 10, which includes a catheter shaft 12 and an inflatable portion or balloon 14 mounted thereon. A medical device, such as a stent 16 is disposed about at least a portion of the balloon 14. The ends 18 and 20 of stent 16 are retained in an unexpanded state by stent retaining sleeves 22 and 24. In addition, overlying the portion of the stent between the sleeves 22 and 24 is a membrane 26.

As is generally known, catheters, including present catheter 10, may be embodied in a variety of configurations and types such as rapid exchange, over the wire, and many other types of catheter arrangements. The present catheter 10 may be any type of catheter suitable for use in a medical device delivery procedure.

The balloon 14 may similarly be embodied in a variety of balloon types. As is know balloons for delivery of medical devices may be composed of one or more materials which may have a variety of material characteristics such as being compliant, non-compliant, elastic, non-elastic, etc. Balloon 14 may be comprised out of any known material or combination of materials, having any variety of characteristics which are suitable for use is medical device delivery. As such the specific materials for constructing the balloon 14 or portions thereof may be, but are not limited to, any of the following materials: thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyetherolyester copolymers, and polyetherpolyamide copolymers. Other suitable materials include a copolymer polyolefin material available from E.I. DuPont de Nemours and Co. (Wilmington, Del.), under the trade name SURLYN™ Ionomer and a polyether block amide available under the trade name PEBAX™. Non-compliant materials include relatively rigid of stiff high pressure polymeric materials, such as thermoplastic polymers and thermoset polymeric materials, poly (ethylene terephthalate) (commonly referred to as PET), polyimide, thermoplastic polyimide, polyamides, polyesters, polycarbonates, polyphenylene sulfides, polypropylene, rigid polyurethanes, Nylon and polyamides.

Stents are well known and understood. In the present invention, stent 16 may be any type of stent. Preferably, stent 16 is a balloon expandable stent, but the invention is directed to the use of self-expanding and hybrid stents as well.

The sleeves 22 and 24 may be manufactured from a variety of materials and may optionally employ a variety of characteristics including holes such as is shown in copending application Ser. No. 09/549,286 as well as others. The sleeves 22 and 24 may optionally employ a wide variety of coatings such as are discussed in copending application Ser. No. 09/427,805. As is known a wide variety of materials may be employed for the manufacture of socks or sleeves depending on the particular characteristics of the delivery device they are to be used with. In the present invention the sleeves 22 and 24 may be made out of any known sleeve material, including but not limited to urethane elastomers.

In the various embodiments shown, the catheter 10 employs a pair of sleeves 22 and 24. However, the present invention may also employ a single sleeve which is associated with a portion of the catheter shaft 14 adjacent to either end 18 or 20 of the stent. Such a sleeve may extend in whole or in-part over the stent 16.

The membrane 26 is a thin layer of material disposed about the stent 16. In the embodiment shown in FIG. 1 the membrane 26 covers the entire surface of the stent 16 which lies between the sleeves 22 and 24. As may be seen from the various figures, the membrane is preferably thinner than the sleeves 22 and 24. Typically, stent retaining sleeves have a thickness less than 0.005 inches. Preferably, the membrane 26 has a thickness less than 0.004 inches and more preferably less than 0.003 inches. In the embodiment shown the thickness of the membrane 26 is 0.002 inches.

Despite the relatively thin character of the membrane 26, the membrane 26 has sufficient strength to retain elements of the stent such as struts, cross-members, and other potentially protruding elements (represented in general by reference numeral 30) from outwardly protruding from the catheter when in the unexpanded state.

Some suitable materials for manufacturing the membrane 26, include but are not limited to thermoplastic elastomers such as KRATON, polystyrene, polyurethanes and any combinations thereof. Other materials which may also be included in the manufacture of the membrane 26 include polytetrafluoroethylene (PTFE) and siloxane.

As shown in FIG. 1 the membrane 26 may cover the entire surface of the stent 16 not already covered by sleeves 22 and 24. Because of the variety of stent configurations which exist it may not be necessary or desirable to cover the entire stent. As may be seen in FIG. 2, the membrane 26, may be seen to cover only a portion of the stent.

Figure 2:
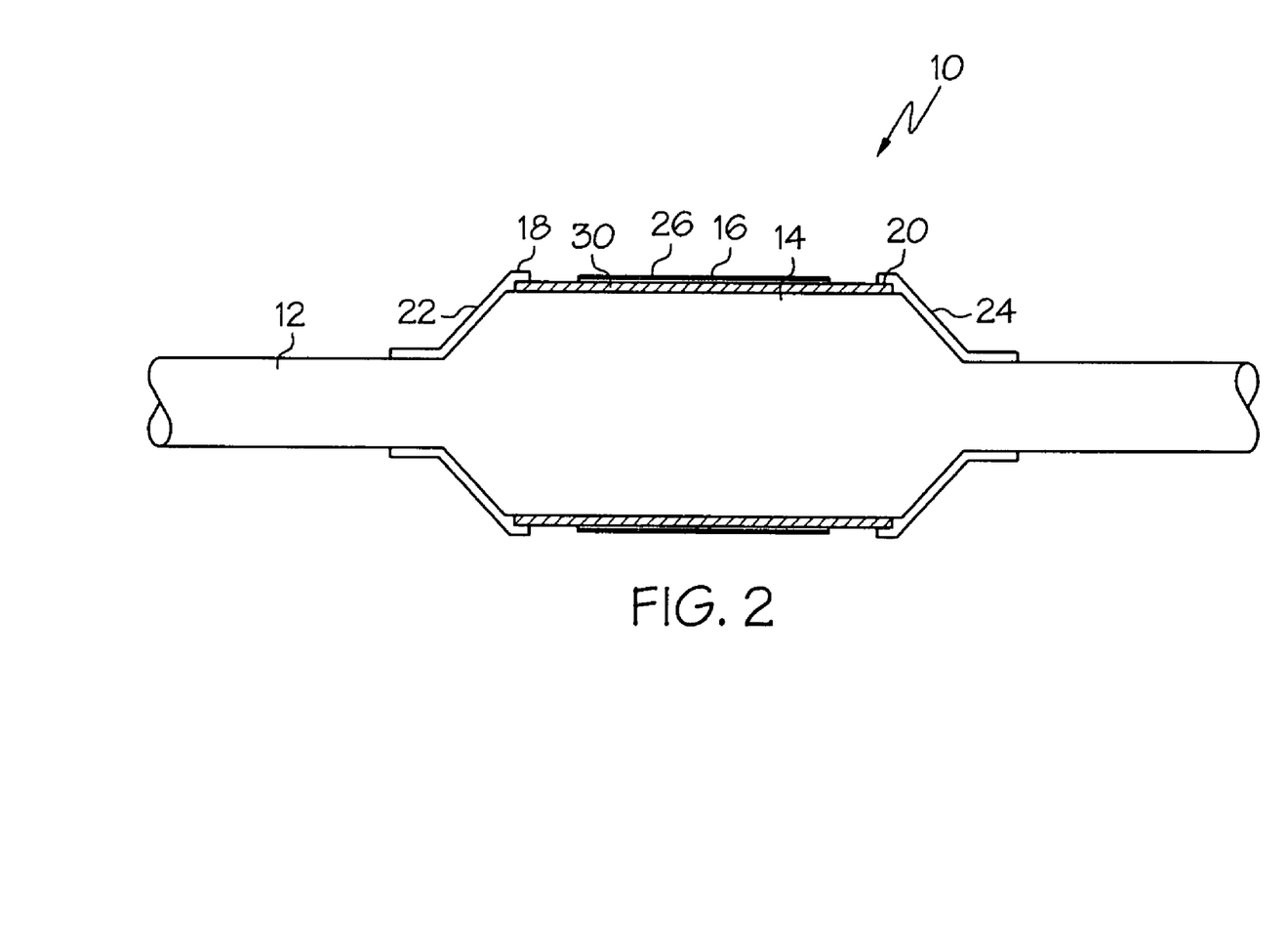
FIG. 2 is a side view of an embodiment of the invention.
Figure 3:
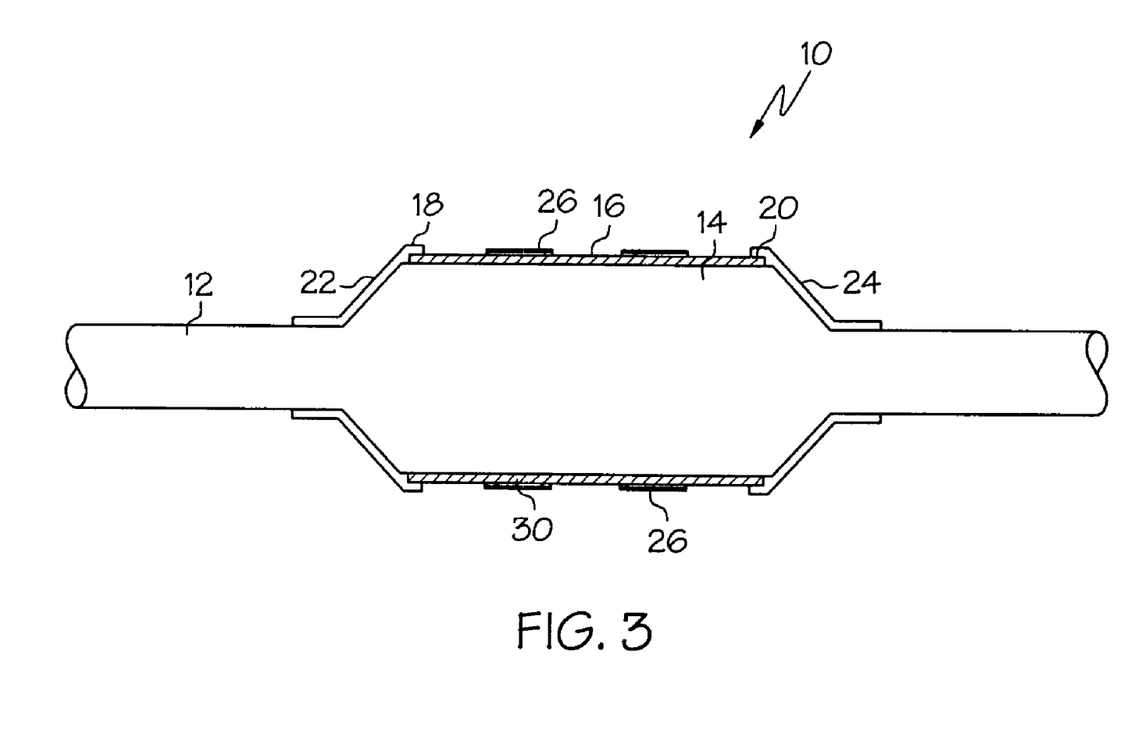
FIG. 3 is a side view of an embodiment of the invention.

In addition to covering the stent 16 in whole or in-part by a single membrane 26 such as is depicted in FIGS. 1 and 2 respectively, the present invention is also directed to selectively covering portions of the stent by utilizing multiple membranes. As may be seen in FIG. 3, the stent 12 is selectively covered with two membranes 26. The number and size of the membrane(s) may be varied as to the characteristics to the individual medical device or stent being deployed. For example, if specific portions of the stent 16 are known to be prone to flaring, membranes of appropriate number and size may be provided to help ensure that the flare prone sections remain in place.

As stated above the membrane(s) may be embodied in a variety of different shapes and sizes. In addition, the membrane may include physical properties to provide increased flexibility. For example, the membrane may be equipped with holes, may be helically disposed about the stent, may be irregularly disposed about the stent, may be partially disposed about the stent or any combination thereof. In addition, the membrane may include one or more lubricants so as to provide for ease of retraction (if retraction is desired).

As previously mentioned, the membrane 26 may be retracted off of the stent 16 prior to delivery of the stent. Alternatively, as may be seen in FIG. 4, the membrane may remain disposed about the stent 16 during and throughout inflation of the balloon 14 and delivery of the stent 16. In the embodiment shown in FIG. 4, the membrane 26 is centrally mounted about a portion of the stent 16 while the stent is in the expanded or delivered state. In such an embodiment where the membrane remains disposed about the stent the membrane may remain in place indefinitely or may be configured to be soluble thereby providing the membrane 26 with the ability to be dissolved by the body subsequent to stent delivery. Such a membrane may be used to delivery drugs to a patient. Drug delivery apparatus are known in the art. An example of which is disclosed in co-pending application PCT/US99/19697.

Figure 4:
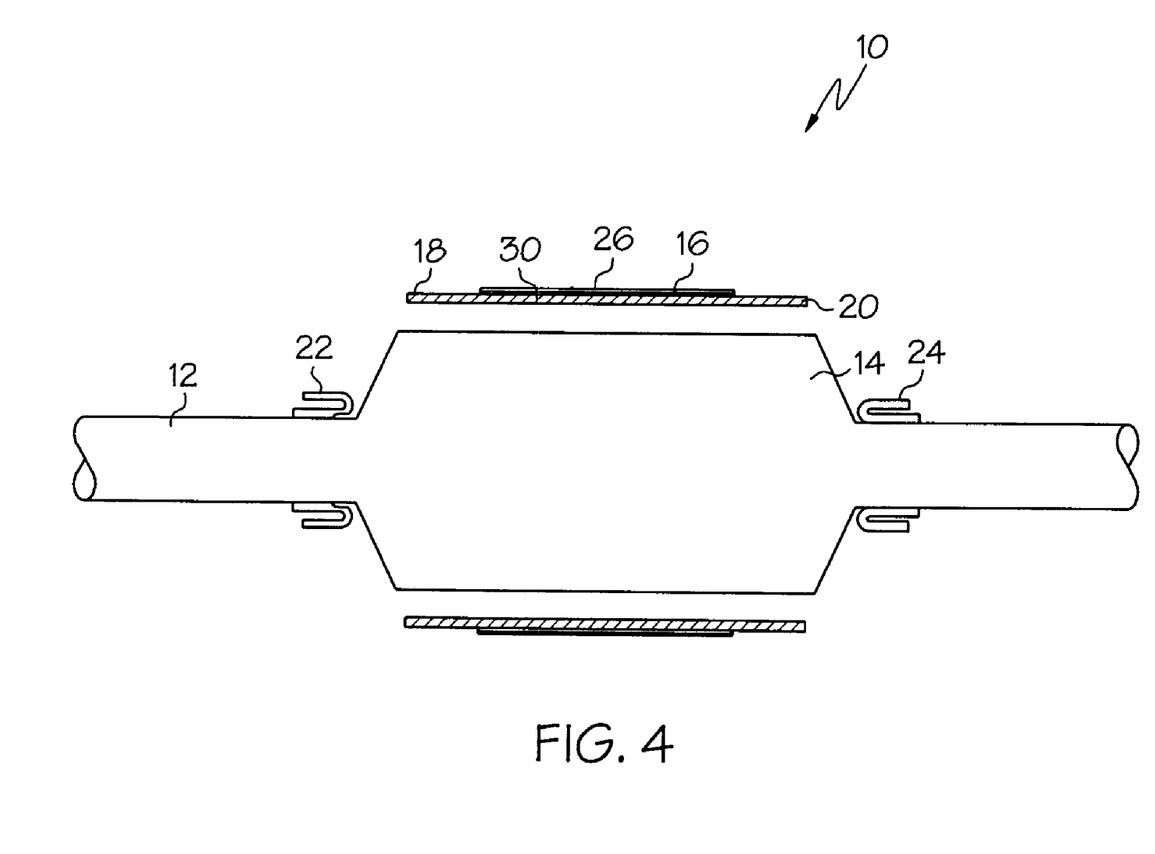
FIG. 4 is a side view of an embodiment of the invention in the expanded state.

As may be seen in FIG. 4 when the balloon 14 is expanded from the unexpanded state (as shown in FIG. 2) to the expanded state, the sleeves 22 and 24 are retracted off of the stent ends 18 and 20 as well as off of the balloon 14.

Figure 5:
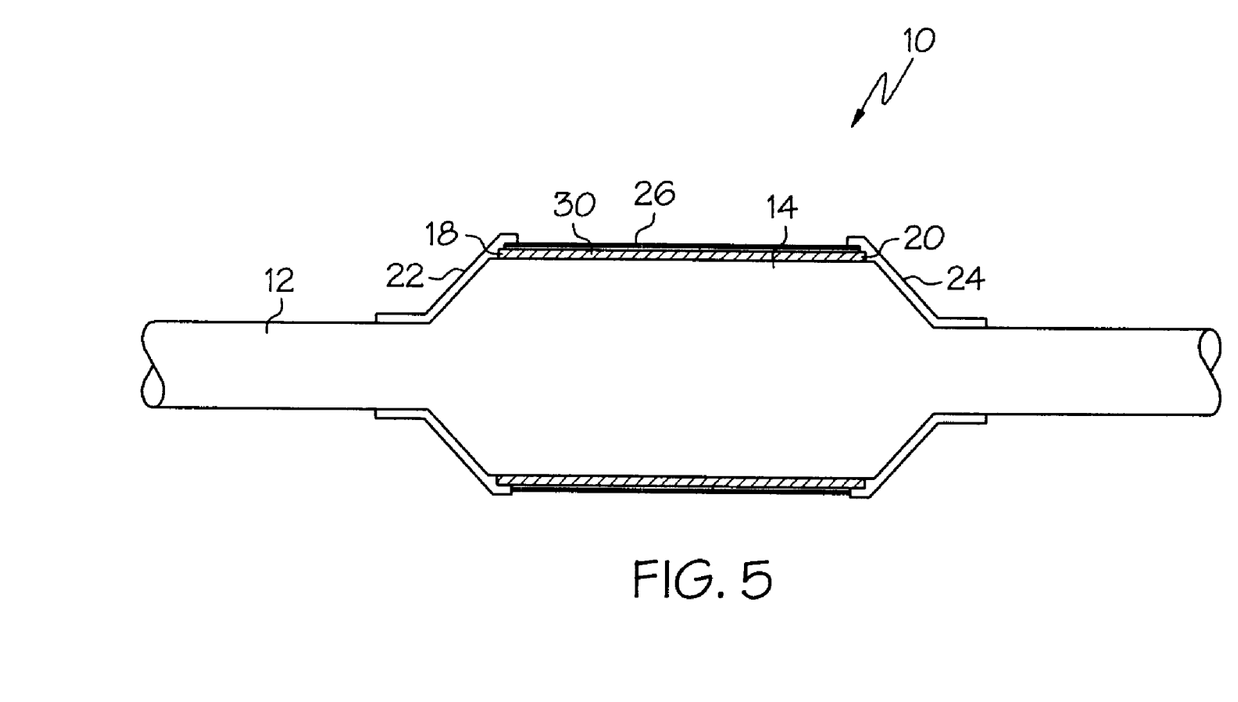
FIG. 5 is a side view of an embodiment of the invention.

Turning to FIG. 5, it may be seen that the membrane 26 may be placed over the entire stent 16. In the embodiment shown, the sleeves 22 and 24 overlap at least the portion of the membrane 26 which in turn overlays the stent ends 18 and 20. Though the additional thickness provided by the membrane 26 does increase the profile of the catheter 10, the increase is negligible due to the extremely thin nature of the membrane as previously discussed.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery system comprising:
a catheter, the catheter having a catheter shaft, the catheter shaft having a balloon mounted thereto;
a stent, the stent disposed about at least a portion of the balloon, the stent having an unexpanded state and an expanded state;
at least one sleeve, the at least one sleeve having a first portion and a second portion, the first portion being engaged to at least a portion of the catheter shaft adjacent to the stent, the second portion at least partially overlaying an end of the stent when the stent is in the unexpanded state;
at least one membrane, at least a portion of the membrane disposed beneath at least a portion of the at least one sleeve, the at least one membrane disposed about at least a portion of the stent, the at least one membrane constructed and arranged to prevent the at least a portion of the stent from flaring outward during advancement of the catheter through a vessel.

2. The stent delivery system of claim 1 wherein the at least one sleeve further comprises a first sleeve and a second sleeve, the stent further comprising a first end and a second end, the second portion of the first sleeve at least partially overlapping the first end of the stent, and the second portion of the second sleeve at least partially overlapping the second end of the stent.

3. The stent delivery system of claim 2 wherein the at least one membrane is disposed about at least a portion of the stent positioned between the second portion of the first sleeve and the second portion of the second sleeve.

4. The stent delivery system of claim 2 wherein the at least one membrane is a plurality of membranes spaced apart axially along the stent.

5. The stent delivery system of claim 2 wherein the second portion of the first sleeve and the second portion of the second sleeve respectively overlying at least a portion of the at least one membrane and an end of the stent.

6. The stent delivery system of claim 1 wherein the at least one membrane is further constructed and arranged to expand with the stent from the unexpanded state to the expanded state.

7. The stent delivery system of claim 6 wherein the at least one membrane is water soluble.

8. A stent delivery system comprising:
a catheter, the catheter having a catheter shaft, the catheter shaft having a balloon mounted thereto;
a stent, the stent disposed about at least a portion of the balloon, the stent having an unexpanded state and an expanded state;
at least one sleeve, the at least one sleeve having a first portion and a second portion, the first portion being engaged to at least a portion of the catheter shaft adjacent to the stent, the second portion at least partially overlaying an end of the stent when the stent is in the unexpanded state;
at least one membrane, the at least one membrane disposed about at least a portion of the stent, the at least one membrane constructed and arranged to prevent the at least a portion of the stent from flaring outward during advancement of the catheter through a vessel;
wherein the at least one membrane is a thermoplastic elastomer.

9. A stent delivery system comprising:
a catheter, the catheter having a catheter shaft, the catheter shaft having a balloon mounted thereto;
a stent, the stent disposed about at least a portion of the balloon, the stent having an unexpanded state and an expanded state;
at least one sleeve, the at least one sleeve having a first portion and a second portion, the first portion being engaged to at least a portion of the catheter shaft adjacent to the stent, the second portion at least partially overlaying an end of the stent when the stent is in the unexpanded state;
at least one membrane, the at least one membrane disposed about at least a portion of the stent, the at least one membrane constructed and arranged to prevent the at least a portion of the stent from flaring outward during advancement of the catheter through a vessel;
wherein the at least one membrane is manufactured from at least one material selected from the group consisting of KRATON, polystyrene, polyurethanes and any combinations thereof.

10. The stent delivery system of claim 9 where in the at least one membrane is additionally manufactured from at least one material of the group consisting of polytetrafluoroethylene, siloxane, and any combinations thereof.

11. A stent delivery system comprising:
a catheter, the catheter having a catheter shall, the catheter shall having a balloon mounted thereto;
a stent, the stent disposed about at least a portion of the balloon, the stent having an unexpanded state and an expanded state;
at least one sleeve, the at least one sleeve having a first portion and a second portion, the first portion being engaged to at least a portion of the catheter shaft adjacent to the stent, the second portion at least partially overlaying an end of the stent when the stent is in the unexpanded state;
at least one membrane, the at least one membrane disposed about at least a portion of the stent, the at least one membrane constructed and arranged to prevent the at least a portion of the stent from flaring outward during advancement of the catheter through a vessel;

wherein the at least one membrane is a drug delivery device.

12. The stent delivery system of claim 1 wherein the at least one membrane has a predetermined membrane thickness and the at least one sleeve has a predetermined sleeve thickness, the predetermined membrane thickness being less than or equal to the predetermined sleeve thickness.

13. A stent delivery system comprising:
   a catheter, the catheter having a catheter shaft, the catheter shaft having a balloon mounted thereto;
   a stent, the stent disposed about at least a portion of the balloon, the stent having an unexpanded state and an expanded state;
   at least one sleeve, the at least one sleeve having a first portion and a second portion, the first portion being engaged to at least a portion of the catheter shaft adjacent to the stent, the second portion at least partially overlaying an end of the stent when the stent is in the unexpanded state;
   at least one membrane, the at least one membrane disposed about at least a portion of the stent, the at least one membrane constructed and arranged to prevent the at least a portion of the stent from flaring outward during advancement of the catheter through a vessel;
   wherein the at least one membrane has a predetermined membrane thickness and the at least one sleeve has a predetermined sleeve thickness, the predetermined membrane thickness being less than or equal to the predetermined sleeve thickness;
   wherein the predetermined membrane thickness is less than 0.005 inches thick.

14. The stent delivery device of claim 13 wherein the predetermined membrane thickness is between about 0.004 and about 0.002 inches thick.

15. A stent delivery system comprising:
   a catheter, the catheter having a catheter shaft, the catheter shaft having a balloon mounted thereto;
   a stent, the stent disposed about at least a portion of the balloon, the stent having an unexpanded state and an expanded state;
   at least one sleeve, the at least one sleeve having a first portion and a second portion, the first portion being engaged to at least a portion of the catheter shaft adjacent to the stent, the second portion at least partially overlaying an end of the stent when the stent is in the unexpanded state;
   at least one membrane, at least a portion of the membrane disposed beneath at least a portion of the at least one sleeve, the at least one membrane disposed about at least a portion of the stent, the at least one membrane constructed and arranged to prevent the at least a portion of the stent from flaring outward during advancement of the catheter through a vessel;
   wherein the at least one sleeve further comprises a first sleeve and a second sleeve, the stent further comprising a first end and a second end, the second portion of the first sleeve at least partially overlapping the first end of the stent, and the second portion of the second sleeve at least partially overlapping the second end of the stent; and
   wherein the at least one membrane is a plurality of membranes spaced apart axially along the stent.

* * * * *